(12) United States Patent
Arramon

(10) Patent No.: US 11,666,460 B2
(45) Date of Patent: Jun. 6, 2023

(54) SURGICAL CUTTER INSTRUMENT WITH TRIAL

(71) Applicant: Simplify Medical Pty Ltd., Melbourne (AU)

(72) Inventor: Yves Arramon, Sunnyvale, CA (US)

(73) Assignee: Simplify Medical Pty Ltd., Melbourne (AU)

( * ) Notice: Subject to any disclaimer, the term of this patent is extended or adjusted under 35 U.S.C. 154(b) by 0 days.

(21) Appl. No.: 17/640,502

(22) PCT Filed: Sep. 23, 2020

(86) PCT No.: PCT/AU2020/000109
§ 371 (c)(1),
(2) Date: Mar. 4, 2022

(87) PCT Pub. No.: WO2021/056044
PCT Pub. Date: Apr. 1, 2021

(65) Prior Publication Data
US 2022/0265284 A1   Aug. 25, 2022

Related U.S. Application Data

(60) Provisional application No. 62/905,070, filed on Sep. 24, 2019.

(51) Int. Cl.
*A61F 2/46* (2006.01)
*A61B 17/16* (2006.01)

(52) U.S. Cl.
CPC ........ *A61F 2/4684* (2013.01); *A61B 17/1604* (2013.01); *A61B 17/1671* (2013.01); *A61F 2/4611* (2013.01); *A61F 2002/4627* (2013.01)

(58) Field of Classification Search
CPC .................................................... A61F 2/4684
See application file for complete search history.

(56) References Cited

U.S. PATENT DOCUMENTS

| 8,852,193 | B2 | 10/2014 | Hushka et al. | |
|---|---|---|---|---|
| 10,888,434 | B2 * | 1/2021 | Adamo | A61F 2/447 |
| 2006/0229627 | A1 | 10/2006 | Hunt et al. | |
| 2007/0233143 | A1 * | 10/2007 | Josse | A61B 17/025 |
| | | | | 606/90 |
| 2009/0198246 | A1 | 8/2009 | Lim et al. | |
| 2017/0202684 | A1 * | 7/2017 | Padovani | A61F 2/4684 |

FOREIGN PATENT DOCUMENTS

| KR | 10-0318703 B1 | 11/2002 |
|---|---|---|
| KR | 1020120025493 A | 3/2012 |

OTHER PUBLICATIONS

Korean Intellectual Property Office, International Search Report and Written Opinion, International Application No. PCT/AU2020/000109, dated Dec. 30, 2020 (15 pages).

* cited by examiner

*Primary Examiner* — Andrew Yang
(74) *Attorney, Agent, or Firm* — Hoffman Warnick LLC

(57) ABSTRACT

Surgical instruments, systems and methods are described for selecting a size and cutting bone for inserting of an intervertebral disc prosthesis. The surgical instrument includes a combined intervertebral disc prosthesis sizing trial and a slot or channel cutter which is movable with respect to the sizing trial.

16 Claims, 5 Drawing Sheets

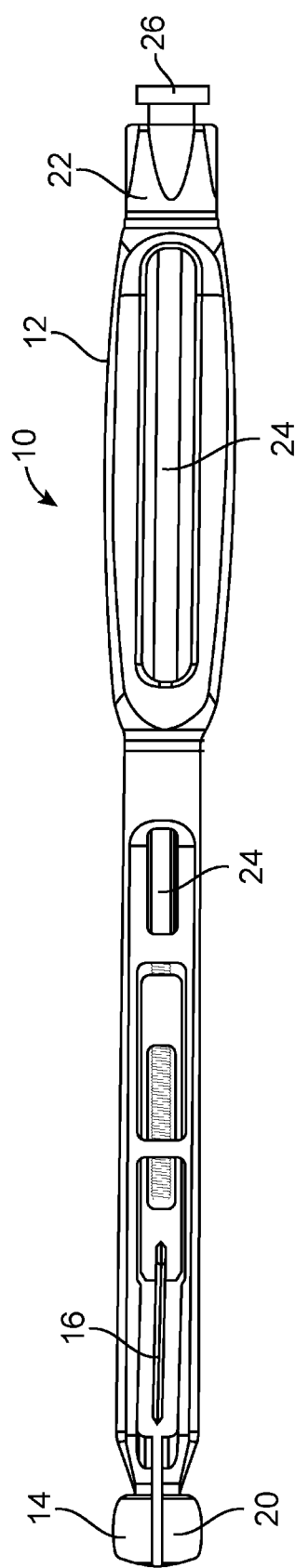
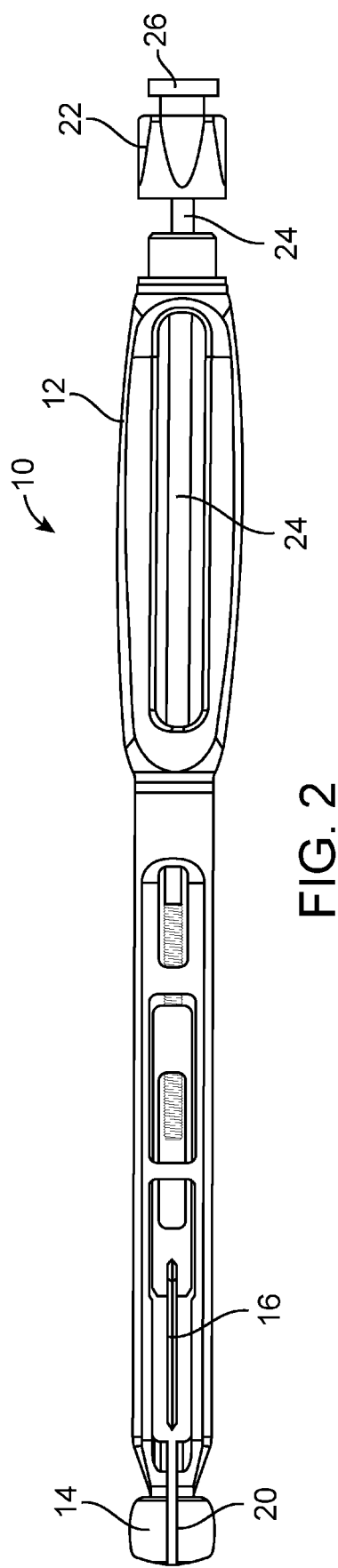

SURGICAL CUTTER INSTRUMENT WITH TRIAL

CROSS-REFERENCE TO RELATED APPLICATIONS

This application is a U.S. national phase under 35 U.S.C. § 371 of International Patent Application No. PCT/AU2020/000109, filed Sep. 23, 2020, which claims the benefit of U.S. Provisional Application No. 62/905,070, filed Sep. 24, 2019, the entire content of which is incorporated herein by reference.

BACKGROUND OF THE INVENTION

1. Field of the Invention

The present invention relates to medical devices, instruments and methods. More specifically, the invention relates to surgical instruments, systems and methods for implantation of an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs. With age, intervertebral disks begin to shrink. In some cases, they may collapse completely and cause the bones to rub against one another. This is referred to as osteoarthritis.

When a damaged intervertebral disc causes a patient pain and discomfort, surgery is often required. Typically, surgical procedures for treating damaged intervertebral discs involve discectomy (partial or total removal of a disc), often followed by interbody fusion of the superior and inferior vertebrae adjacent to the disc or implantation of an intervertebral prosthetic disc.

Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together. Spinal fusion eliminates motion between the vertebrae. Fusion is an option when motion is the source of pain. However, fusion limits a patient's spinal mobility and can create additional stresses on adjacent spinal segments.

An alternative to spinal fusion which doesn't limit patient mobility is total disc replacement (TDR), also called total disc arthroplasty. The TDR procedure involves removing the natural disk from between the vertebrae and replacing it with an artificial disc prosthesis. Several types of intervertebral disc prosthesis are currently available. For example, one type of intervertebral disc prosthesis includes upper and lower prosthesis plates which locate against and engage the adjacent vertebral bodies and a mobile core positioned between the plates. The core may be movable or fixed, metallic, ceramic or polymer and generally has at least one convex outer surface which mates with a concave recess on one of the plates in a fixed core device. In a movable core device one or both of the outer surfaces of the core may be curved. In order to implant these intervertebral discs, the natural disc is removed and the vertebrae are distracted or forced apart in order to fit the artificial disc in place. The plates may be inserted individually or together and with or without a core. However, it is desirable to reduce the duration of the procedure by implanting the disc in an assembled configuration and in as few steps as possible.

Currently available intervertebral prosthetic discs are held, delivered and removed with a variety of different instruments and techniques. Depending on the particular disc design, one or more channels or slots may need to be cut into the vertebral bodies adjacent the disc space to accommodate one or more fins or teeth of the intervertebral prosthetic disc. These channels are cut by one or more cutting tools specifically designed for the TDR procedure. However, challenges with these known cutting instruments and techniques include excessively time consuming, complicated techniques of use and difficulty is precise positioning of the cuts. It would be desirable to provide a disc system with a cutting instrument which can be used for both sizing/positioning the prosthetic disc and cutting the bone in preparation for insertion of the prosthetic disc.

In addition, it would be desirable to provide a cutting instrument which also serves as a trial for determining the appropriate implant size.

Therefore, a need exists for an improved artificial intervertebral disc placement instruments, systems and methods which improve speed and reliability of the surgical procedures.

2. Description of the Background Art

A variety of intervertebral disc prosthesis designs and methods of implanting are described in described in U.S. Pat. Nos. 7,442,211; 7,531,001; 7,575,599; 7,585,326; 7,637,913; 7,753,956; 8,206,449; 8,685,035; 8,764,833; 8,808,384; 9,011,544 and 9,351,846, and U.S. patent application Ser. Nos. 15/842,663 and 62/841,359, each of which is incorporated herein by reference in its entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is a top view of a surgical cutter instrument with the cutting blade in a retracted and locked position;

FIG. 2 is a top view of the instrument of FIG. 1 with the cutting blade in a retracted and released position;

DETAILED DESCRIPTION OF THE INVENTION

Figure 3:
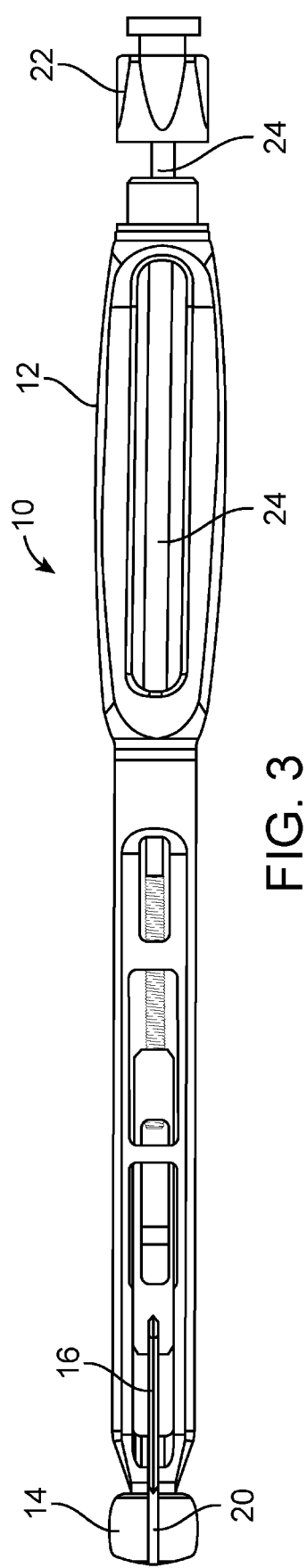
FIG. 3 is a top view of the instrument of FIG. 1 with the cutting blade partly advanced and ready for cutting.

Positioning of an intervertebral prosthetic disc properly in the spine is an important part of a successful total disc arthroplasty (TDR) procedure. The position of the implant in the intervertebral space can influence the range of motion, implant behavior and clinical result. Proper positioning of the disc between the vertebral bodies is important but can be difficult due to lack of visibility and surrounding anatomy. Surgeon experience, surgeon training, bone preparation techniques, use of imaging modalities and patient anatomy are all factors which can influence accuracy of prosthetic disc placement.

Prior to placing an intervertebral prosthetic disc between two vertebral bodies in the spine, the surgeon prepares the disc space to receive the disc. Disc space preparation may include removal of the natural disc with surgical instruments and cutting and shaping bone with bone cutting instruments. When the intervertebral prosthetic disc to be placed includes projections such as fins, teeth or keels, a surgeon may cut one or more grooves, slots or other cuts in the vertebra to receive these projections. The surgeon may also use one or more trial implants or implant sizers during the process of preparing the disc space to receive the disc. The trial implants match the shape and size of available prosthetic discs and are inserted into the prepared disc space to determine which disc size should be selected.

After the trial process is complete and a disc size has been selected, a cutting instrument can be used to cut the one or more slots or channels in the vertebral bodies. Cutting instruments can include one or more cutting blades on the distal end of an instrument handle designed to be impacted by a mallet to advance the cutting blades into the bone.

FIG. 1 illustrates a first embodiment of a surgical cutter instrument 10 according to the present invention. In addition to functioning as a surgical cutter, the instrument 10 is also designed for use as a trial. In one embodiment, the cutter instrument 10 is provided in a set which includes multiple size cutter instruments which correspond to the sizes of the intervertebral discs available for implant.

The cutter instrument 10 includes a handle 12, a trial sizer head 14, and one or more movable cutting blades 16. The trial sizer head 14 is shaped and sized to match available implant sizes and has a longitudinal slot 20 in both the upper (superior) surface and the lower (inferior) surface (not shown) which allows the cutting blade 16 to be advanced into the vertebral bone. The cutting blade 16 is movable in a longitudinal direction between the retracted position of FIG. 1 and a fully advanced position in which a distal end of the cutting blade is substantially advanced to a distal edge of the sizer head 14. In FIG. 1, the cutting blade 16 is in a retracted position and is locked in the retracted position by threading a proximal handle nut 22 onto the proximal end of the handle 12. The proximal handle nut 22 is configured to be impacted by a mallet if needed to insert the trial sizer head into the disc space. The cutting blade 16 is connected to the proximal handle nut 22 by a longitudinal shaft 24 extending through the instrument.

FIG. 2 illustrates the cutter instrument 10 with the cutting blade 16 unlocked in preparation for cutting bone. The cutting blade 16 is unlocked or released by loosening the proximal handle nut 22 until it is no longer locked to the handle 12. With the cutting blade 16 in the released or unlocked position, the cutting blade can be advanced distally on the instrument. The cutting blade 16 is preferably released after the trial sizer head 14 has been inserted into the disc space and confirmed to be the correct size of implant to be inserted. The disc shaped thumb button 26 of the proximal handle nut 22 provides a surface for advancing both the trial and the cutter.

Figure 7:
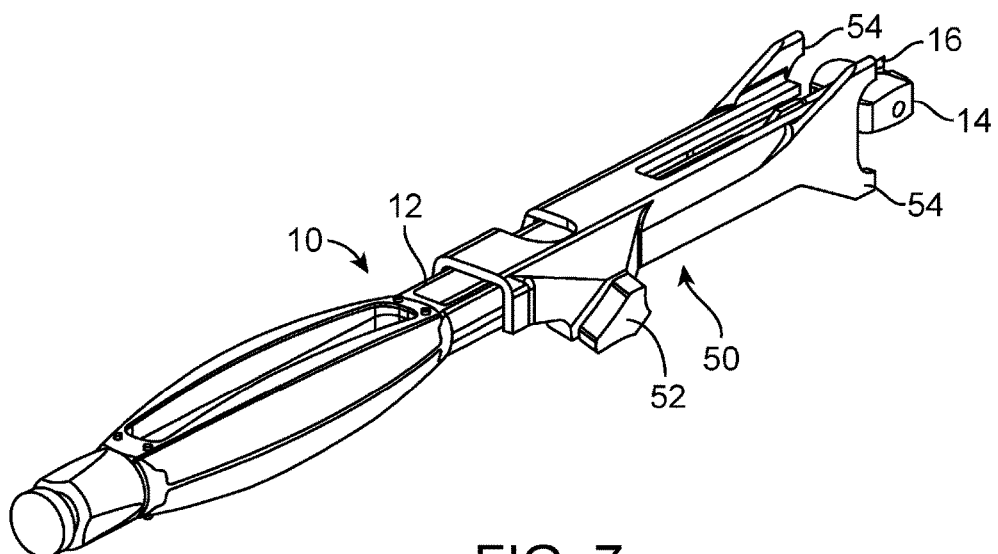
FIG. 7 is a perspective view of an alternative embodiment of a surgical cutter instrument with a removable stop.
Figure 8:
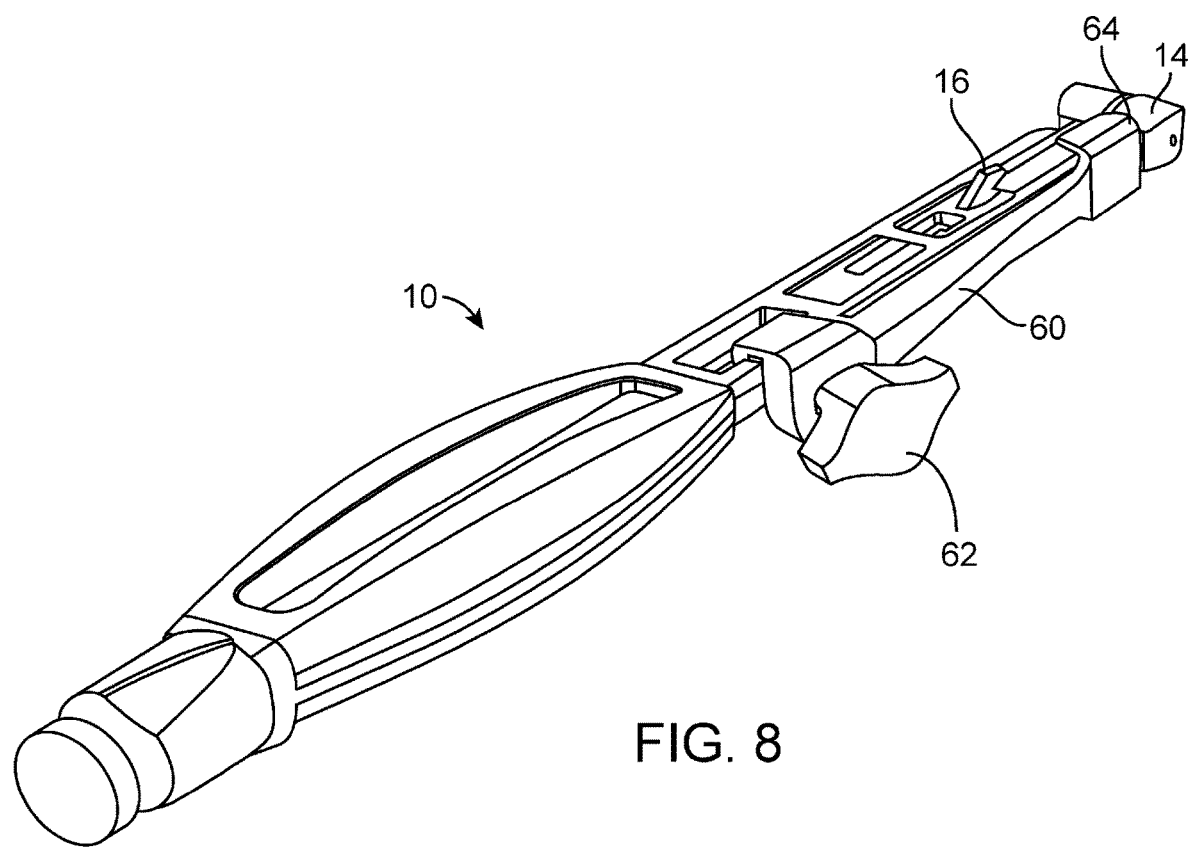
FIG. 8 is a perspective view of an alternative embodiment of a surgical cutter instrument with a side removable stop.

FIG. 3 illustrates the cutting blade 16 advanced distally until a distal end of the cutting blade is adjacent the bone and ready for cutting. Cutting is performed by impacting the proximal handle nut 22 with a mallet to advance the cutting blade into the bone while holding the trial sizer head 14 stationary. A proximal stop on the cutter instrument 10 or attachable to the cutter instrument (as shown in FIGS. 7 and 8) can be used to hold the trial sizer head 14 stationary during cutting and prevent the trial sizer head 14 from moving posteriorly during advancement of the cutting blade.

Figure 4:
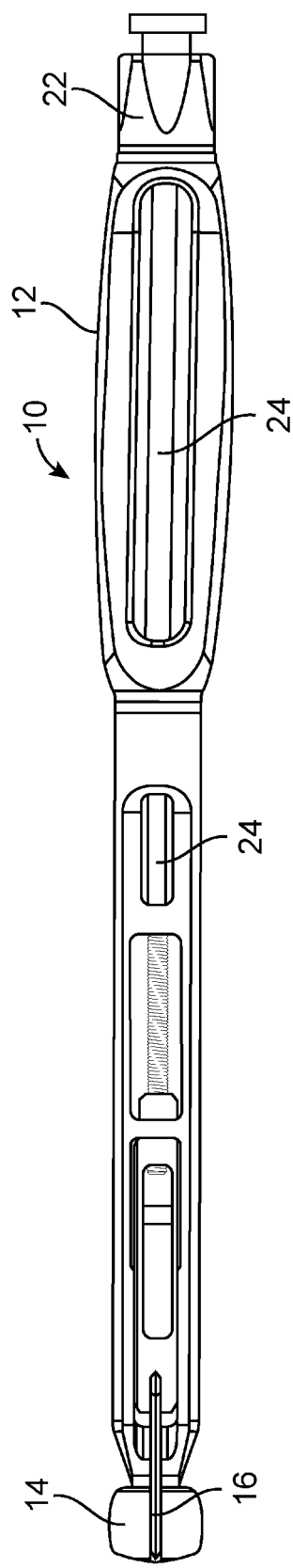
FIG. 4 is a top view of the instrument of FIG. 1 with the cutting blade in the fully advanced position.

FIG. 4 illustrates the cutting blade 16 advanced all the way distally in the position in which the bone cut is fully complete and the instrument is ready to be removed from the disc space. The various windows provided in the cutter instrument 10 including in the handle 12 are provided for purposes of allowing cleaning of the instrument. The windows also allow the shaft 24 connected to the cutter blade 16 and the nut 22 to be visible within the instrument.

Figure 5:
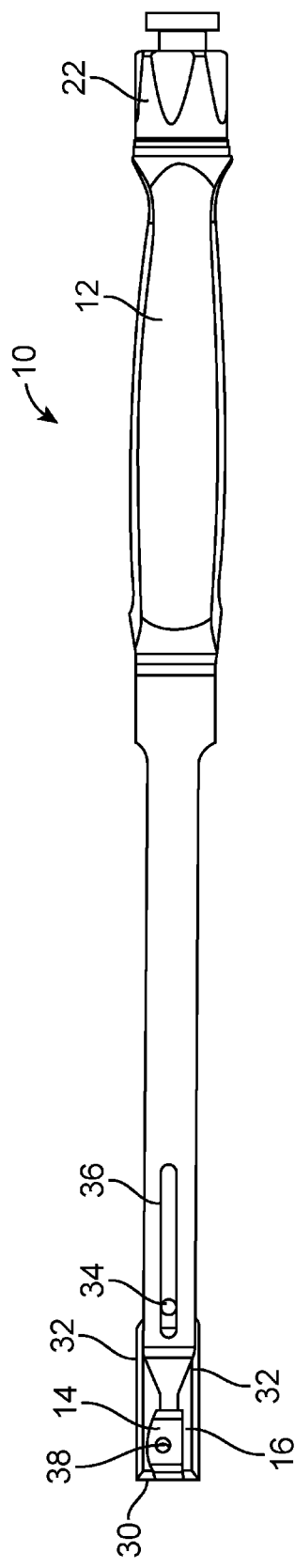
FIG. 5 is a side view of the instrument of FIG. 1 with the cutting blade in the fully advanced position of FIG. 4.
Figure 6:
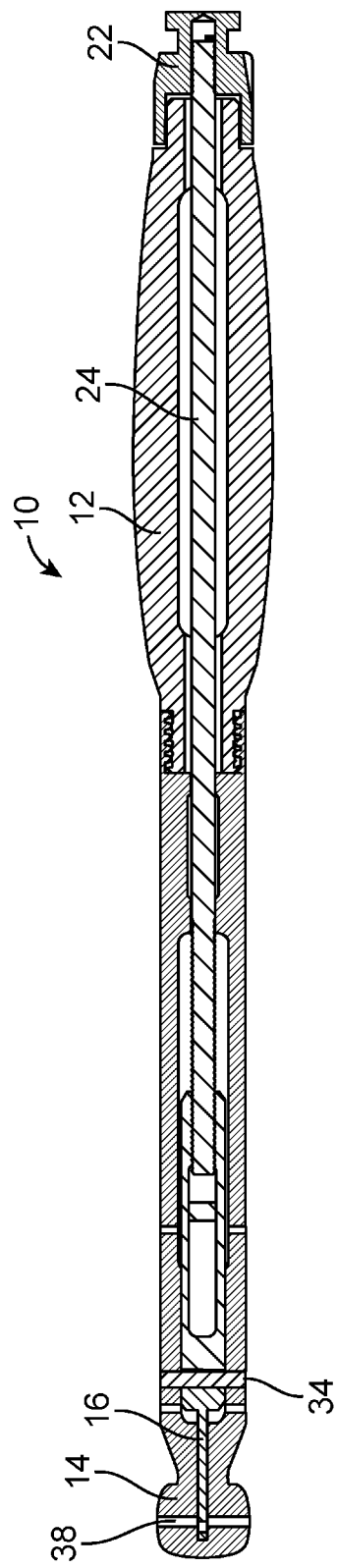
FIG. 6 is a cross sectional top view of the instrument of FIG. 1.

FIG. 5 is a side view of the instrument 10 with the cutting blade 16 in the fully advanced position of FIG. 4. The details of the cutting blade 16 can be seen more clearly in FIG. 5. Although cutting blades can vary in shape, the cutting blade 16 shown includes a perpendicular beveled distal cutting end 30 and parallel upper and lower beveled cutting edges 32. The beveled cutting edges can be replaced with serrated edges and the perpendicular distal cutting end 30 can be replaced with forward or backward angled blade tips. The cutting blade 16 is secured to the shaft 24 with the pin 34 (seen in FIGS. 5 and 6) which slides within a slot 36 in the shaft 12.

Also shown in FIG. 5 is a through hole 38 in the trial sizer head 14 which is positioned centered in the anterior/posterior direction for aligning the trial sizer head 14 in the disc space under X-ray or fluoroscopy.

FIG. 7 illustrates the combined trial and cutting instrument 10 of FIG. 1 with the addition of a removable stop 50 attached to a shaft 24 of the instrument. The removable stop 50 is attached around the instrument shaft, longitudinally adjustable and secured in place by a screw locking mechanism 52 or other locking mechanism. The removable stop 50 can be positioned on the instrument shaft 24 after the correct trial sizer head has been selected and positioned in the disc space in preparation for cutting. The distal end of the removable stop 50 has one or more and preferably four bone stop surfaces 54 positioned to abut a surface of the vertebrae, such as the anterior surfaces of the vertebrae above and below the implantation level near the sides of the vertebrae. The removable stop 50 is configured to limit motion of the trial sizer head 14 and the cutter blade 16 to safely cut the slots without over insertion.

FIG. 8 illustrates an alternative removable stop 60 attached to a shaft 24 of the instrument. The removable stop 60, also referred to herein as bone stop 60, is attached around one side wall of the instrument shaft, is longitudinally adjustable on the side wall and secured in place by a screw locking mechanism 62 or other locking mechanism. The distal end of the removable stop 60 has one or more and preferably one bone stop surface 64 positioned to abut an anterior surface on one side of both the upper and lower vertebrae. Although a single bone stop 60 is shown, two bone stops may also be used on the two sides of the instrument shaft 24. The bone stop 60 leaves a center of the shaft 24 uncovered for an unobstructed view to the midline of the vertebrae and the cutting blade 16.

Figure 9:
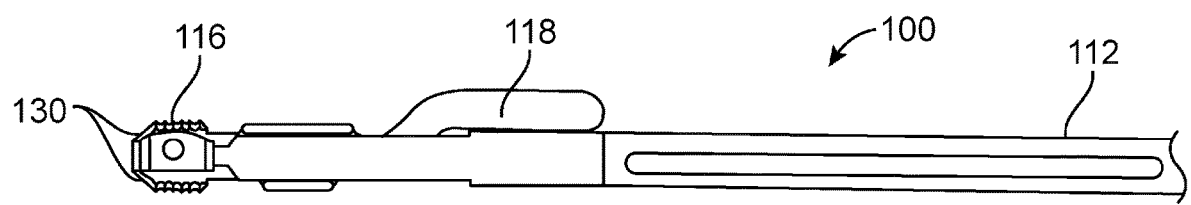
FIG. 9 is a side view of an alternative embodiment of a surgical cutter instrument with a removable blade in a cutting position.
Figure 10:
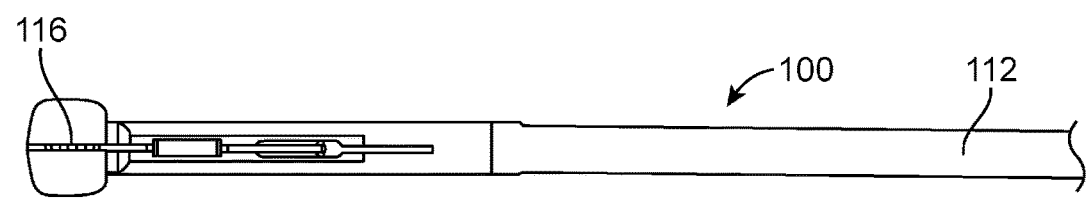
FIG. 10 is a top view of the instrument of FIG. 8 with the cutting blade in the cutting position.

FIGS. 9 and 10 show a side and a top view, respectively, of an alternative embodiment of a cutting instrument 100 having a removable cutting blade 116 attached to a cutter handle 118 which allows the cutting blade 116 to be inserted into a slot in the instrument and removed from the instrument for cleaning and storage. In the example of FIGS. 8 and 9, the cutting blade 116 has parallel serrated cutting edges and backward angled distal cutting ends 130. The cutting instrument 100 can be used as a trial to determine the implant size to be selected. The trial is removed and then the removable blade 116 is locked into place in the instrument and the cutting is performed. This is different from the method of using the cutting instrument 10 which does not require that the instrument be removed from the patient to begin the cutting step. Additionally, the removal of the cutting blade 116 from the instrument shaft 112 facilitates cleaning of the instrument either manually or mechanically.

In the embodiment of FIGS. 1-6, the retracted and unlocked position of the cutting instrument 10 shown in FIG. 2 is both the position for beginning cutting during surgery and is the cleaning position for the instrument once surgery is complete. In the cleaning position, the nut 22 is fully unthreaded or disengaged from threads at the proximal end of the handle 12, however, the nut 22 does not fall off the instrument since it is prevented from fully separating from the instrument by connection to the shaft 24. In the cleaning position, all parts of the instrument 10 are connected and unable to be completely separated and are in a loose configuration to allow cleaning fluid to pass through all parts of the instrument. Cleaning windows in the handle 12 and in the instrument outer shaft assist in allowing cleaning fluid to circulate through all parts of the instrument.

The combination trial and cutter instruments 10, 100 described herein can be used in a surgical method with the steps of sequentially inserting one or more different size combined trial and cutter instruments into a vertebral disc space to check a fit of the trial for the disc space; unlocking a cutter on a selected combined trial and cutter instrument while the cutter is in the disc space to allow the cutter to be movable with respect to the trial; and cutting bone of at least one of the bones adjacent to the vertebral disc space with the cutter by moving the cutter distally with respect to the trial.

Although surgical instruments, systems and methods have been described for use in preparation of vertebrae to accommodate an intervertebral disc prosthesis, the systems and methods described herein may also be used for improved precision and optimal performance of other spinal implants including interbody fusion devices or vertebral body replacements. The surgical systems and methods can be used to assist the surgeon in improving the accuracy and speed of these other surgical procedures. Additionally, the surgical instruments, systems and methods can be used for anterior cervical disc replacement as well as for anterior, posterior or lateral lumbar intervertebral disc prosthesis procedures. With lumbar disc procedures and other disc approaches the shape and size of the trial and cutter would be modified to match these approaches to and locations in the spine.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. A surgical cutting instrument comprising:
   an instrument shaft having a distal end and a proximal end;
   an instrument handle on the proximal end of the instrument shaft;
   a trial sizer head configured to attach to the distal end of the instrument shaft and to correspond in size to an intervertebral implant, wherein the trial sizer head comprises at least one longitudinal slot; and
   a cutter configured to attach to the instrument shaft and axially translatable within the at least one longitudinal slot in the trial sizer head,
   wherein in a retracted and locked position, the cutter is positioned proximally of the trial sizer head and is locked in position.

2. The surgical cutting instrument of claim 1, wherein the instrument shaft includes an inner shaft and an outer shaft movable with respect to one another.

3. The surgical cutting instrument of claim 2, wherein the cutter is configured to attach to the inner shaft.

4. The surgical cutting instrument of claim 1, wherein in a released cutting position, the cutter is movable with respect to the trial sizer head into and through the at least one longitudinal slot.

5. The surgical cutting instrument of claim 1, wherein the at least one longitudinal slot extends along a midline of the instrument between two opposite lateral edges.

6. The surgical cutting instrument of claim 1, wherein the at least one longitudinal slot comprises a pair of slots on opposite superior and inferior surfaces of the trial sizer head.

7. The surgical cutting instrument of claim 1, further comprising a removable adjustable stop attachable to the instrument shaft and configured to limit motion of the trial sizer head.

8. A set of surgical cutting instruments according to claim 1, comprising a plurality of surgical cutting instruments each having a different size trial sizer head.

9. A surgical method comprising:
   inserting a first combined trial sizer head and cutter instrument into a vertebral disc space to check a fit of the first trial sizer head for the vertebral disc space, wherein the vertebral disc space is disposed adjacent to at least two bones;
   removing the first combined trial sizer head and cutter from the vertebral disc space and inserting a second combined trial sizer head and cutter instrument of a different size; and
   unlocking a cutter on the second combined trial sizer head and cutter instrument to allow the cutter to be axially translatable with respect to the trial sizer head; and
   cutting at least one of the bones adjacent to the vertebral disc space with the cutter.

10. The surgical method of claim 9, wherein the cutting step comprises cutting a slot into at least one of the bones adjacent to the vertebral disc space.

11. The surgical method of claim 10, wherein the slot is a midline slot.

12. The surgical method of claim 9, further comprising attaching a removable adjustable stop to the second combined trial sizer head and cutter instrument and limiting motion of the trial sizer head during cutting by contacting at least one of the bones adjacent to the vertebral disc space with the adjustable stop.

13. A surgical method of cutting bone for insertion of an intervertebral disc prosthesis, the surgical method comprising:
   sequentially inserting one or more different size combined trial sizer head and cutter instruments into a vertebral disc space to check a fit of the trial sizer head for the vertebral disc space;
   unlocking a cutter on a selected combined trial sizer head and cutter instrument while the cutter is in the vertebral disc space to allow the cutter to be movable with respect to the trial sizer head; and
   cutting at least one of the bones adjacent to the vertebral disc space with the cutter by moving the cutter distally with respect to the trial sizer head.

14. The surgical method of claim 13, wherein the cutting step comprises cutting a slot into at least one of the bones adjacent to the vertebral disc space.

15. The surgical method of claim 14, wherein the slot is a midline slot.

16. The surgical method of claim 13, further comprising attaching a removable adjustable stop to the combined trial sizer head and cutter instrument and limiting motion of the trial sizer head during cutting by contacting at least one of the bones adjacent to the vertebral disc space with the adjustable stop.

\* \* \* \* \*